United States Patent [19]
Bertelmann et al.

[11] 4,271,190
[45] Jun. 2, 1981

[54] GUANIDINIUM SALTS, PROCESSES FOR THEIR MANUFACTURE AS WELL AS MICROBICIDAL PREPARATIONS CONTAINING THESE COMPOUNDS

[75] Inventors: Günter Bertelmann; Ulrich Holtschmidt; Arnold Laqua, all of Essen, Fed. Rep. of Germany

[73] Assignee: Th. Goldschmidt AG, Essen, Fed. Rep. of Germany

[21] Appl. No.: 141,184

[22] Filed: Apr. 17, 1980

Related U.S. Application Data

[63] Continuation of Ser. No. 16,409, Mar. 1, 1979, abandoned.

[30] Foreign Application Priority Data

Mar. 2, 1978 [DE] Fed. Rep. of Germany ....... 2808943

[51] Int. Cl.$^3$ .................. A61K 31/205; C07C 129/12
[52] U.S. Cl. .................................... 424/316; 424/326; 260/501.14; 564/240
[58] Field of Search ...................... 260/501.14, 564 F; 424/316, 326; 564/240

[56] References Cited
U.S. PATENT DOCUMENTS

| | | | |
|---|---|---|---|
| 3,201,459 | 8/1965 | Coda et al. | 260/564 F |
| 3,202,710 | 8/1965 | Bolger | 260/564 F |
| 3,291,829 | 12/1966 | Mull | 260/501.14 |

OTHER PUBLICATIONS

Pasini et al., "Chem. Absts.", 66, 2449(x), 1967.
Crowther et al., "Chem. Absts.", 62, 9023(b), 1965.
McKay et al., J. of Medicinal Chemistry, vol. 6, pp. 587–595 (1963).

*Primary Examiner*—G. T. Breitenstein
*Attorney, Agent, or Firm*—Toren, McGeady and Stanger

[57] ABSTRACT

Guanidinium salts having the formula

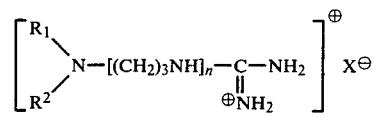

wherein
$R^1$ and $R^2$ are linear alkyl residues,
X is an anion, and
n is 1 or 2, which possess excellent microbicidal properties, particularly against organisms which have become resistant against other active materials. Methods for preparation of the compounds and solutions containing same are disclosed.

14 Claims, No Drawings

GUANIDINIUM SALTS, PROCESSES FOR THEIR MANUFACTURE AS WELL AS MICROBICIDAL PREPARATIONS CONTAINING THESE COMPOUNDS

This is a continuation of application Ser. No. 016,409, filed on Mar. 1, 1979, now abandoned.

BACKGROUND OF THE INVENTION

1. Field of the Invention

This invention relates to compounds which are guanidinium salts suitable for use in microbicidal compositions.

2. Description of the Prior Art

The bactericidal effectiveness of guanidines and salts of guanidine is already well known. A detailed summary may be found in the "Journal of Medicinal Chemistry", Vol. 6 (1963), pages 587 to 595.

German Auslegeschrift 12 49 457 discloses that salts of alkyl diguanidines of the general formula

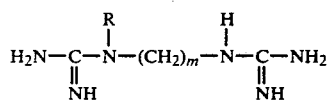

in which R represents an alkyl radical of 8 to 18 carbon atoms and m a number from 2 to 6, may be used as microbicides.

In German Offenlegungsschrift No. 26 47 915, partial reaction products of aliphatic polyamines with guanidizing agents are described. However, one of the problems that have been encountered with these compounds is that strains have developed which have high resistance to them. Thus, the microbicidal effectiveness of these compounds has decreased.

In practical operations, the chlorohexidine derivatives have especially proven their value as gaunidine derivatives. These correspond to the following formula

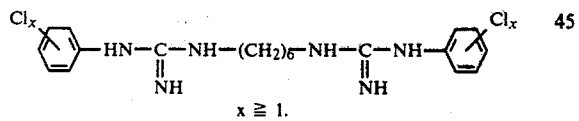

These compounds, which are sold under the trade name "Chlorohexidine", have excellent bactericidal effectiveness. However, they suffer from the disadvantage that their biological degradation leads to chlorinated aromatic compounds, which resist further biological degradation and are highly toxic and can poison, for example, biological sewage treatment operations. These compounds are expensive to manufacture and their use has up till now been limited to precision disinfection.

SUMMARY OF THE INVENTION

We have discovered a new series of compounds which do not exhibit the organism resistance possessed by known guanidine derivatives, which degrade to non-toxic materials, and which are relatively inexpensive.

More particularly, the new compounds of the present invention have the general formula

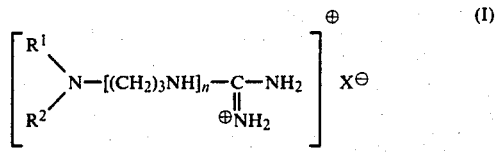

In this formula, $R^1$ and $R^2$ are the same or different and represent linear alkyl residues with 8 to 16 carbon atoms. X is an anion, for example sulfate, acetate, lactate or gluconate. The choice of anion is optional. It is dictated essentially by the required solubility of the compounds and by the intended application. For example, the acetates of these compounds are more readily soluble than the sulfates. If the compounds are used in microbicidal preparations, a physiologically safe anion, such as, for example, the aforementioned organic anions, is preferred. If the anion is divalent or multivalent, the cationic portion of the compounds is present twice or several times in the molecule.

The index n is equal to 1 or 2.

The new compounds may be prepared simply and by known procedures. The starting materials are geminal, substituted, dialkyl polyamines of the formula

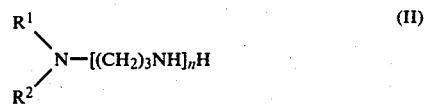

In the process of the present invention, these alkylated polyamines are reacted with (a) at least half molar amounts of the compound

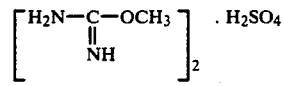

or (b) at least molar amounts of the compound

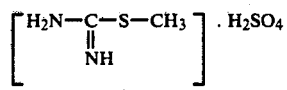

in aqueous and/or alcoholic solution, optionally at elevated temperatures. The products of the process, optionally after concentration by evaporation, are separated by filtration, centrifuging or other procedures suitable for separating a solid product from an aqueous and/or alcoholic solution, or (c) at least equimolar amounts of cyanamide in dilute, aqueous acetic acid, optionally in the presence of additional organic solvents at elevated temperature. Subsequently, the acetic acid, water, and any organic solvent contained are distilled off.

DESCRIPTION OF THE PREFERRED EMBODIMENT

The process, referred to as (a) proceeds at room temperature. It is, however, advisable to work at elevated temperatures in order to accelerate the reaction. Suitable elevated temperatures are those from 30° to 50° C. In the case of the process referred to as (b), it is advisable to allow the reaction to proceed at the boiling point of the reaction mixture.

Water may be used as the reaction medium. Instead of water, lower aliphatic alcohols, such as, ethanol, propanol, butanol or mixtures of these alcohols with water may be used.

The desired guanidine salt precipitates as a moderately soluble sulfate and can be separated from the solution by filtration or centrifuging. Obviously, it is also possible to use any other procedure which is suitable for separating a solid substance from a liquid medium. The mother liquor can be returned to the cycle. Additional portions of the guanidinium salt may be obtained by evaporative concentration.

Procedure (a) may be described by the following reaction sequence

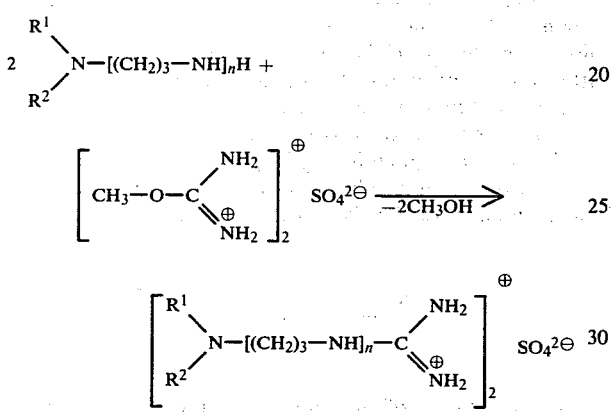

Procedure (b) similarly corresponds to the following reaction sequence

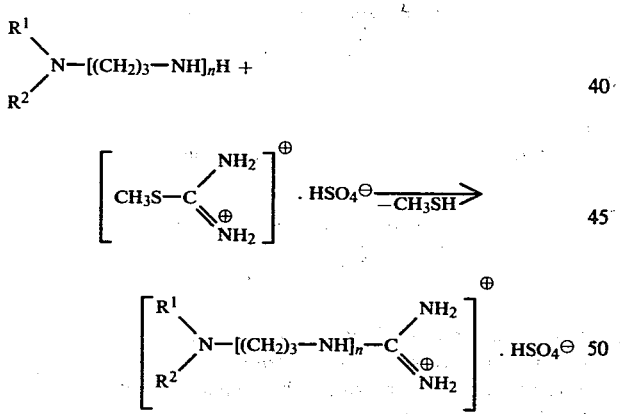

The conversion of the guanidinium sulfate obtained into a different salt, e.g., the acetate, may be accomplished by reaction with the corresponding calcium or barium salt.

Procedure (c) consists of reacting the alkylated polyamine of Formula II with cyanamide. For this purpose, at least one mole of cyanamide should be used for each mole of the polyamine. The reaction is carried out in dilute, aqueous acetic acid. Additional organic solvents, such as, lower aliphatic alcohols with 1 to 4 carbon atoms, or cyclic ethers, such as, for example, dioxane, may be added. The reaction preferably is carried out at elevated temperatures.

The reaction temperature is determined by the boiling point of the reaction mixture unless the solvents used permit a temperature of up to 95° C. to be chosen. At the conclusion of the reaction, the acetic acid, together with water and any organic solvents therein is distilled of.

Procedure (c) may be described by the following reaction sequence:

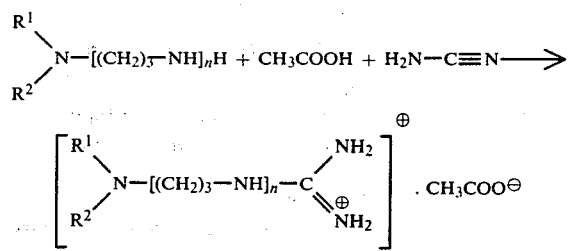

The new compounds have excellent microbicidal properties. These microbicidal properties are largely retained when these compounds act on a substrate in the presence of a soap or protein, e.g., serum.

It is an essential characteristic of the new compounds of this invention that they contain previously unknown combinations of the groups

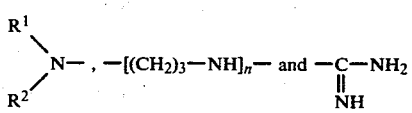

($R^1$ and $R^2$=linear alkyl residues with 8 to 16 carbon atoms) which admittedly by themselves are known in microbicidal substances, but which, through the association in a single molecule, endow this molecule with independent properties from the point of view of resistance behavior. Similar phenomena are known in the case of antibiotics in which, particularly in the case of the representatives containing the semi-synthetic β-lactam groups, it is possible to master resistance phenomena which occur, by introducing other types of groups or substituents in the molecule.

In their microbicidal effect, the inventive compounds are at least equivalent to other substances of the state of the art. Their use opens up the possibility of being able to combat effectively once again those strains which had become resistant towards other active materials; by the timely change to different active substances, it is even possible to forestall the development of resistance. Accordingly, the availability of a new, highly effective microbicide represents a valuable advance in the fight against disease-causing organisms, food spoilers and other harmful microbes.

The inventive compounds on the other hand are readily biodegradable. Since the geminal substituted polyamines are inexpensive and readily obtainable, the inventive compounds may also be used more generally in less specific disinfection.

The invention therefore also relates to microbicide preparations, which are characterized by their content of effective compounds of the general formula I, in addition to the usual manufacturing materials.

Manufacturing refers to the production of applicable preparations, for example, the production of aqueous solutions of the inventive compounds in concentrated form or at a concentration in which they are typically used. Manufacturing also includes the adjustment to a specific pH value appropriate for the intended application, the possible addition of known cationic or non-ionic surface active substances in order to decrease the surface tension of these solutions and/or to increase their cleaning action, and, optionally, the coloration and/or the perfuming of the preparation.

A different form of manufacturing consists of producing a dry product, in which case the pure crystalline substance is used or the pure substance is mixed especially with inorganic inert carriers. Such carriers are, for example, water soluble, physiologically safe inorganic salts or insoluble carriers, such as, silicic acids or clays, such as, bentonite for example. Recently, the dissolving of active substances in low-boiling solvents and the spraying of the solutions of the active substances by means of compressed gas has also gained in importance. These forms of preparation are marketed as aerosols.

As mentioned above, cationic or nonionic surface-active substances may be added to the compounds of the present invention. Suitable as cationic compounds are, for example, quaternary ammonium compounds, such as, cetyl pyridinium chloride or benzalkonium chlorides, which also have the property of enhancing the activity of the inventive compound. The well-known addition products of ethylene oxide with compounds with an acidic hydrogen, especially with alcohols with 8 to 14 carbon atoms, may be used as nonionic compounds.

In the following examples, the synthesis of the new compounds is shown and their microbicidal effectiveness is demonstrated.

The microbiological effectiveness of the new compounds was determined by suspension tests corresponding to the guidelines of the Deutsche Gesellschaft für Hygiene und Mikrobiologie (German Association for Hygiene and Microbiology) (3rd edition, 1972). *Staphylococcus aureus, Escherichia coli, Proteus vulgaris* and *Pseudomonas aeruginosa* were used as test organisms. The threshold effectiveness concentration (in ppm corresponding to γ/ml) of the inventive microbicidal compounds, at which a definite germicidal effect is observed, is recorded for periods of ten minutes and twenty-four hours.

Concentration levels of 0.5, 1, 5, 10,50 and 100 ppm, corresponding to γ/ml, were used. Intermediate concentrations were not checked. For example, if the value of 10 ppm is given for the threshold effectiveness concentration, this means that a definite germicidal effect is not assured at 5 ppm; the limiting concentration may lie, however, in the range between 5 and 10 ppm.

The inventive compounds generally may be synthesized by processes such as the following.

I. Guanidizing Reaction with O-Methyl Isourea Sulfate

A mixture of 2 moles N,N-difattyalkyl propylene diamine or N,N-difattyalkyl dipropylene triamine with 1,000 ml of water is stirred. A solution of 0.96 moles of O-methyl isourea sulfate in 400 ml of water is added with stirring. The temperature of the mixture rises slowly to 25° to 30° C. When the exothermic reaction has ended, the reaction batch is heated at 50° C. for 2 hours. The guanidinium salt suspension formed is freed from water and methanol in a rotary evaporator and the residue remaining is purified by washing with ether. After drying over $P_2O_5$ in a vacuum oven, the desired product is obtained in a sufficiently pure form.

II. Guanidizing reaction with S-Methyl Isothiourea Sulfate

A mixture of 1 mole of N,N-difattyalkyl propylene diamine or N,N-difattyalkyl dipropylene triamine, 1.3 moles of S-methyl isothiourea sulfate and 1000 ml alcohol were heated with efficient stirring for 6 hours at the boiling point under reflux. The heterogeneous reaction mixture was cooled, the precipitated crystals were filtered off with suction, the crystalline reaction product washed well with alcohol and dried in a vacuum oven. The corresponding guanidinium sulfate was obtained in a sufficiently pure form without further recrystallization.

III. Guanidizing Reaction with Cyanamide

A mixture of 1 mole of N,N-difattyalkyl propylene diamine or N,N-difattyalkyl dipropylene triamine and 460 ml of water is heated with stirring to 70° C. in a reaction flask. From a dropping funnel, 0.6 moles of acetic acid are added slowly. An exothermic reaction takes place, during which the temperature of the reaction mixture rises to about 85° C. The addition of 0.1 ml of a defoamer, e.g., a silicone emulsion, is advisable. Heating is continued to 95° C.

Over a period of one hour, a mixture of 1.6 moles cyanamide (270 g of a 25% aqueous solution) and 0.3 moles of acetic acid are run in from a dropping funnel. The reaction mixture then is heated for 3½ hours at 98° C. to 100° C. The pH is controlled and maintained at a value of 8 by the addition of acetic acid. For this purpose, about 0.05 moles of acetic acid are used. For the purpose of isolating the reaction product, the acetic acid and water are largely distilled off.

The precipitate of the respective guanidinium acetate is filtered off with suction, washed with water and dried in a vacuum over $P_2O_5$. The product may be recrystallized from water.

IV. Conversion of the Guanidinium Sulfate Obtained from Processes I or II into the Acetate A solution of 1 mole of guanidinium sulfate in 1000 ml of ethanol is heated to boiling. A hot solution of 1 mole of the alkaline earth salt with the desired anion, e.g., barium acetate, in 1000 ml of water is added dropwise from a heated addition funnel to the suspension of the guanidinium sulfate. After the addition, the mixture is heated for a further 15 minutes under reflux and then allowed to cool slowly over night. The precipitated alkaline earth sulfate is filtered off, the filtrate concentrated by evaporation in a rotary evaporator and the guanidinium acetate thus obtained dried in a vacuum oven over $P_2O_5$.

EXAMPLE 1

(a) Synthesis of the sulfate of 1-dioctylamino-3-guanidinopropane

Using the procedure of Process I, 590 g (2 moles) of 1-dioctylamino-3-guanidino-propane are reacted with 236 g (0.96 moles) of O-methylisourea sulfate. After working up the reaction batch, 651 g (83.7% of the theoretical yield) of guanidinium sulfate are obtained.

Analysis for $C_{40}H_{90}N_8O_4S$

| Calculated | | Found | |
| --- | --- | --- | --- |
| C | 61.7% | C | 61.0% |
| H | 11.6% | H | 11.8% |

-continued

| Calculated | | Found | |
|---|---|---|---|
| N | 14.4% | N | 14.1% |
| $SO_4^{2-}$ | 12.3% | $SO_4^{2-}$ | 12.8% |

(b) Synthesis of the acetate of 1-dioctylamino-3-guanidino-propane

Using the general procedure of Process IV, 778 g (1 mole) of the sulfate of the compound 1-dioctylamino-3-guanidino-propane are reacted with 255 g (1 mole) of barium acetate. The working up of the batch produces 784 g (98% of the theoretical yield) of guanidinium acetate.

Analysis for $C_{22}H_{48}N_4O_2$

| Calculated | | Found | |
|---|---|---|---|
| C | 66.0% | C | 65.4% |
| H | 12.1% | H | 12.0% |
| N | 14.0% | N | 13.4% |
| O | 7.9% | O | 8.5% |

(c) Testing the microbiological effectiveness of compounds synthesized according to (a) and (b)

By dissolving guanidinium salts in distilled water, 10% test solutions with a pH of about 7 were prepared. Dilute acetic acid or sodium hydroxide was used for adjusting the pH. The sulfate of the 1-dioctylamino-3-guanidino-propane has reached its upper solubility limit as a 10% aqueous solution.

Microbiological test results are

| Test Organisms | Effective Concentration in ppm after a Period of Action of | | | |
|---|---|---|---|---|
| | 10 Minutes | | 24 Hours | |
| | (a) sulfate | (b) acetate | (a) sulfate | (b) acetate |
| S. aureus | 50 | 10 | 1 | 0.5 |
| E. coli | 100 | 50 | 5 | 5 |
| P. vulgaris | 50 | 50 | 5 | 5 |
| P. aeruginosa | 50 | 50 | 10 | 5 |

EXAMPLE 2

(a) Synthesis of the sulfate of 1-didecylamino-3-guanidino-propane

Using the procedure of Process I, 708 g (2 moles) of 1-didecylamino-3-amino-propane are reacted with 236 g (0.96 moles) of O-methylisourea sulfate. The working up of this batch resulted in 623 g (70% of the theoretical yield) of guanidinium sulfate.

Analysis for $C_{48}H_{106}N_8O_4S$

| Calculated | | Found | |
|---|---|---|---|
| C | 64.7% | C | 65.0% |
| H | 12.0% | H | 12.2% |
| N | 12.6% | N | 12.1% |
| $SO_4^{2-}$ | 10.7% | $SO_4^{2-}$ | 10.3% |

(b) Synthesis of the acetate of 1-didecylamino-3-guanidino-propane

Using the procedure of Process IV, 890 (1 mole) of the sulfate of the compound 1-didecylamino-3-guanidino-propane are reacted with 255 g (1 mole) of barium acetate. After the batch was worked up, 866 g (95% of the theoretical yield) of the corresponding guanidinium acetate were obtained.

Analysis for $C_{26}H_{56}N_4O_2$

| Calculated | | Found | |
|---|---|---|---|
| C | 68.4% | C | 67.9% |
| H | 12.4% | H | 12.4% |
| N | 12.3% | N | 12.0% |
| O | 6.9% | O | 6.8% |

(c) Testing the microbiological effectiveness of compounds synthesized according to (a) and (b)

As in Example 1 (c), 10% aqueous solutions adjusted to a neutral pH, were used in the tests. As expected, the solubility of the guanidinium sulfate in water is considerably less than the solubility of the acetate.

Microbiological test results:

| Test Organisms | Effective Concentration in ppm after a Period of Action of | | | |
|---|---|---|---|---|
| | 10 Minutes | | 24 Hours | |
| | (a) Sulfate | (b) Acetate | (a) Sulfate | (b) Acetate |
| S. aureus | 10 | 10 | 1 | 0.5 |
| E. coli | 10 | 50 | 5 | 5 |
| P. vulgaris | 10 | 50 | 5 | 5 |
| P. Aeruginosa | 50 | 50 | 10 | 10 |

EXAMPLE 3

(a) Synthesis of the sulfate of 1-dioctylamino-4-aza-7-guanidino-heptane

Using the procedure of Process I, 710 g (2 moles) of 1-dioctylamino-4-aza-7-amino-heptane are reacted with 236 g (0.96 moles) of O-methylisourea sulfate. The working up of this reaction batch leads to 535 g (60% of the theoretical yield) of the desired guanidinium sulfate.

Analysis for $C_{46}H_{104}N_{10}O_4S$

| Calculated | | Found | |
|---|---|---|---|
| C | 61.8% | C | 61.2% |
| H | 11.7% | H | 12.0% |
| N | 15.7% | N | 15.3% |
| S | 3.6% | S | 3.7% |

(b) Synthesis of the acetate of 1-dioctylamino-4-aza-7-guanidino-heptane

Using the procedure of Process IV, 892 g (1 mole) of the sulfate of the compound 1-dioctylamino-4-aza-guanidino-heptane are reacted with 255 g (1 mole) of barium acetate. After working up the batch, 850 g (93% of the theoretical yield) of the corresponding guanidinium acetate are obtained.

Analysis for $C_{25}H_{55}N_5O_2$

| Calculated | | Found | |
|---|---|---|---|
| C | 65.6% | C | 65.2% |
| H | 12.1% | H | 12.0% |
| N | 15.2% | N | 14.9% |
| O | 7.1% | O | 7.0% |

(c) Testing the microbiological effectiveness of compounds synthesized according to (a) and (b)

Because of its poor solubility in water, the guanidinium sulfate could be used only as a 1% neutral test solution. The guanidinium acetate was used as a 10% neutral aqueous test solution.

Microbiological test results:

| Test Organisms | Effective Concentration in ppm after a Period of Action of | | | |
| --- | --- | --- | --- | --- |
| | 10 Minutes | | 24 Hours | |
| | (a) Sulfate | (b) Acetate | (a) Sulfate | (b) Acetate |
| S. aureus | 100 | 50 | 5 | 1 |
| E. coli | 50 | 50 | 10 | 5 |
| P. vulgaris | 100 | 50 | 5 | 5 |
| P. aeruginosa | 10 | 10 | 10 | 5 |

EXAMPLE 4

(a) Synthesis of the sulfate of 1-didecylamino-4-aza-7-guanidino-heptane

Using the procedure of Process II, a mixture of 822 g (2 moles) of 1-didecylamino-4-aza-7-amino-heptane, 488 g (2.6 moles) of S-methylisothiourea sulfate and 2000 ml of alcohol are boiled for 6 hours under reflux with good stirring. After working up the heterogeneous reaction mixture according to the general procedure, 773 g (77% of the theoretical yield) of the sulfate of the compound 1-didecylamino-4-aza-7-guanidino-heptane were obtained.

Analysis for $C_{54}H_{120}N_{10}O_4S$

| Calculated | | Found | |
| --- | --- | --- | --- |
| C | 64.5% | C | 64.0% |
| H | 12.0% | H | 12.2% |
| N | 13.9% | N | 13.8% |
| S | 3.2% | S | 3.3% |

(b) Synthesis of the Acetate of 1-didecylamino-4-aza-7-guanidino-heptane

Using the procedure of Process IV, 1004 g (1 mole) of the sulfate of the compound 1-didecylamino-4-aza-7-guanidino-heptane are reacted with 255 g (1 mole) of barium acetate. The working up of the batch leads to 975 g (95% of the theoretical yield) of the acetate of the compound 1-didecylamino-4-aza-7-guanidino-heptane.

Analysis for $C_{29}H_{63}N_5O_2$

| Calculated | | Found | |
| --- | --- | --- | --- |
| C | 69.1% | C | 68.5% |
| H | 10.6% | H | 10.8% |
| N | 13.9% | N | 13.4% |
| O | 6.4% | O | 6.9% |

(c) Testing the microbiological effectiveness of compounds synthesized according to (a) and (b)

Because of its poor solubility in water, the guanidinio sulfate is used for the microbiological testing as a 1% neutral, aqueous solution, while the corresponding guanidinium acetate is used as a 10% neutral, aqueous solution.

Microbiological test results:

| Test Organisms | Effective Concentration in ppm after a Period of Action of | | | |
| --- | --- | --- | --- | --- |
| | 10 Minutes | | 24 Hours | |
| | (a) Sulfate | (b) Acetate | (a) Sulfate | (b) Acetate |
| S. aureus | 50 | 10 | 1 | 0.5 |
| E. coli | 50 | 50 | 5 | 5 |
| P. vulgaris | 50 | 10 | 5 | 1 |
| P. aeruginosa | 50 | 50 | 5 | 5 |

EXAMPLE 5

(a) Synthesis of the sulfate of 1-octyl-decyl-amino-4-aza-7-guanidino-heptane

Using the procedure of Process I, 766 g (2 moles) of the compound 1-octyl-decyl-amino-4-aza-7-amino-heptane are reacted with 236 g (0.96 moles) of O-methylisourea sulfate. After working up the reaction mixture, 616 g (65% of the theoretical yield) of the sulfate of the compound 1-octyl-decyl-amino-4-aza-7-guanidino-heptane were obtained.

Analysis of $C_{50}H_{112}N_{10}O_4S$

| Calculated | | Found | |
| --- | --- | --- | --- |
| C | 61.0% | C | 60.5% |
| H | 11.9% | H | 11.8% |
| N | 12.9% | N | 12.3% |
| S | 4.3% | S | 4.1% |

(b) Synthesis of the acetate of 1-octyl-decyl-amino-4-aza-7-guanidino-heptane

Using the procedure of Process III, 383 g (1 mole) of 1-octyl-decyl-amino-4-aza-7-amino-heptane in aqueous acetic acid solution are reacted with 67 g (1.6 moles) of cyanamide (dissolved in dilute acetic acid). The guanidinium acetate, obtained from working up the batch, is recrystallized once from water in order to increase its purity. The acetate of the compound 1-octyl-decyl-amino-4-aza-7-guanidino-heptane is obtained in a yield of 363 g, corresponding to 75% of the theoretical yield)

Analysis for $C_{27}H_{59}N_5O_2$

| Calculated | | Found | |
| --- | --- | --- | --- |
| C | 66.9% | C | 66.4% |
| H | 12.2% | H | 12.0% |
| N | 14.3% | N | 14.1% |
| O | 6.6% | O | 6.4% |

(c) Testing the microbiological effectiveness of compounds synthesized according to (a) and (b)

The guanidinium sulfate is used as a 1% neutral, aqueous solution. The corresponding acetate is used as a 10% neutral aqueous solution for the test.

Microbiological test results:

| Test Organisms | Effective Concentration in ppm after a Period of Action of | | | |
| --- | --- | --- | --- | --- |
| | 10 Minutes | | 24 Hours | |
| | (a) Sulfate | (b) Acetate | (a) Sulfate | (b) Acetate |
| S. aureus | 10 | 5 | 1 | 0.5 |
| E. coli | 10 | 10 | 5 | 5 |
| P. vulgaris | 10 | 5 | 5 | 1 |
| P. aeruginosa | 50 | 10 | 5 | 5 |

What is claimed is:

1. A compound having the formula

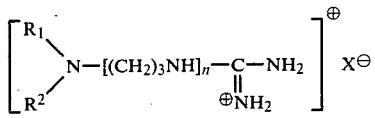

in which the substituents
R¹ and R² are the same or different and represent linear alkyl residues with 8 to 16 carbon atoms,
X is an anion, and
n is 1 or 2.

2. The compound of claim 1 wherein the anion is selected from the group consisting of sulfate, lactate, acetate, and gluconate.

3. 1-dioctylamino-3-guanidino-propane sulfate.
4. 1-dioctylamino-3-guanidino-propane acetate.
5. 1-didecylamino-3-guanidino-propane sulfate.
6. 1-didecylamino-3-guanidino-propane acetate.
7. 1-dioctylamino-4-aza-7-guanidino-heptane sulfate.
8. 1-dioctylamino-4-aza-7-guanidino-heptane acetate.
9. 1-didecylamino-4-aza-7-guanidino-heptane sulfate.
10. 1-didecylamino-4-aza-7-guanidino-heptane acetate.
11. 1-octyldecylamino-4-aza-7-guanidino-heptane sulfate.
12. 1-octyldecylamino-4-aza-7-guanidino-heptane acetate.

13. A microbicidal preparation containing a microbicidally effective amount of the compound of claim 1 and a carrier therefor.

14. A method for sterilizing a substrate comprising applying a microbicidally effective amount of a composition composed of the compound of claim 1 and a carrier therefor.

* * * * *